(12) United States Patent  (10) Patent No.:  US 6,909,359 B1
McGovern  (45) Date of Patent:  Jun. 21, 2005

(54) REAL-TIME MEDICAL ALERTING SYSTEM

(76) Inventor: Robert T. McGovern, 42 Heatherwood Dr., Colchester, CT (US) 06415

( * ) Notice: Subject to any disclaimer, the term of this patent is extended or adjusted under 35 U.S.C. 154(b) by 44 days.

(21) Appl. No.: 10/407,583

(22) Filed: Apr. 4, 2003

(51) Int. Cl.$^7$ ................................................ G08B 1/00
(52) U.S. Cl. ............................. 340/309.16; 340/286.02; 340/286.07
(58) Field of Search .................. 340/309.16, 286.02, 340/286.07, 311.2; 364/479.01

(56) References Cited

U.S. PATENT DOCUMENTS

| | | | | |
|---|---|---|---|---|
| 5,612,869 A | * | 3/1997 | Letzt et al. ...................... 705/3 |
| 5,623,242 A | * | 4/1997 | Dawson et al. ............... 340/7.3 |
| 5,824,180 A | * | 10/1998 | Mikuni et al. ............ 156/275.3 |
| 5,850,344 A | * | 12/1998 | Conkright .................... 700/231 |
| H1782 H | * | 2/1999 | Wicks et al. .................. 340/7.2 |
| 5,954,641 A | * | 9/1999 | Kehr et al. ................... 600/300 |
| 6,075,755 A | * | 6/2000 | Zarchan ........................ 368/10 |
| 2003/0086338 A1 | * | 5/2003 | Sastry et al. .................. 368/10 |

* cited by examiner

*Primary Examiner*—Daniel Wu
*Assistant Examiner*—Son Tang
(74) *Attorney, Agent, or Firm*—Jeffrey C. Lew

(57) ABSTRACT

A computerized reminder system collates medical prescription information such as provided by commercial retail pharmacies to customized schedules for administration of medication and therapy to patients. The system broadcasts reminder information via radio frequency wireless transmissions over a wide area network subsystem to portable receivers uniquely associated with specific patients. The patients receive real-time reminders directed only to them to take medicine. Patients receive only their own respective reminders and do not obtain reminders for other patients who subscribe to the system.

21 Claims, 1 Drawing Sheet

REAL-TIME MEDICAL ALERTING SYSTEM

FIELD OF THE INVENTION

This invention relates to a system and method for timely reminding a medical patient concerning prescribed regimens for the administration of medications or medical therapies. More specifically it pertains to a real-time prescription reminding service which monitors medical prescription information about one or more patients and broadcasts reminders over a wide area networks to receivers selective for picking up reminders addressed to specific individual patients to whom the reminders are addressed.

BACKGROUND OF THE INVENTION

In the modern age, the use of prescribed medications to combat illnesses of all types is becoming increasingly complicated. This is due to many factors including the proliferation of medicines. In addition to multiple medications for well known and common diseases, there are now available and forthcoming medicines for a variety of ailments for which pharmaceutical therapy had not previously been available. The administration of these many pharmaceutical products is further complicated by the fact that often medications are used in combination to treat an illness. Therefore a patient is required to take multiple medications for a single condition.

This situation is still further complicated by the unfortunate circumstance that many patients are beset with multiple simultaneous health problems. Because there may be more than one medicine for each health issue, the patient can be forced to take a large number of different medications for periods of time. The Centers for Disease Control and Prevention currently reports that patient's over 65 typically are given 15 medical prescriptions per year and that 6 of these are for recurring prescriptions meant for continued administration of medications for the management of chronic conditions.

The amount and frequency of dosage are other problematic concerns. It is more the rule than the exception that each medication is prescribed to be taken at dosage levels and times different from others. Thus it becomes almost hopelessly difficult to track the correct schedule for taking multiple medications. This has been documented in an article titled: *A systematic review of the associations between dose regimens and medication compliance* [Claxton, A J; Cramer, J; Pierce, C Clin Ther. 2001 August; 23(8): 1296 310]. The review indicated that mean non-compliance across 76 studies in general was 29%, however, non-compliance increased to 49% among persons who took at least 4 medications. According to the Merck Manual of Medical Information/Home Edition, citing the Office of the United States Inspector General, noncompliance with drug treatment annually results in 125,000 deaths from cardiovascular disease, up to 23 percent of nursing home admissions, 10 percent of hospital admissions, many doctor visits, many diagnostic tests, and many unnecessary medical treatments. A study titled: *Drug related medical emergencies in the elderly: role of adverse drug reactions and non compliance*, [Malhotra, S; Karan, R S; Pandhi, P; Jain, S Postgrad Med J. 2001 November; 77(913): 703–7] asserts that 7.6% of all hospital admissions among the elderly were related to medication non-compliance. Perhaps the most well known example of this issue relates to the pharmaceutical therapy of Acquired Immune Deficiency Syndrome (AIDS). Some AIDS patients are prescribed to follow exacting regimens calling for the administration of at least three different medicine taken at different times around the clock for extended durations of therapy. The consequences of deviating from these regimens can be tragic.

Another factor that makes the use of modem prescription drugs difficult is the possibly adverse interaction between certain pharmaceutical products and allergic reactions to which some patients are susceptible. It is not uncommon for patients with multiple ailments to consult specialists for each health condition. Unless each doctor is aware of the medications that other physicians are simultaneously prescribing, the same patient can receive a prescription for a conflicting medicine. The medications themselves may have a cross reaction or a second medicine can have an aggravating effect on a different health condition for which the patient is currently being treated.

It is of course common to retain strong mental powers well into advanced age. However, memory loss among older persons is a general malaise. Considering that health problems tend to increase with age, it follows that the segment of population most likely to use pharmaceuticals is that which in general has intrinsic difficulty tracking the details of complex medical prescriptions.

For the reasons set forth above, there is a deeply felt need for a system that helps a user of pharmaceutical products be reminded to take the proper medicine at the proper time. Such a system which also has the ability to maintain and provide an up to the minute report of all prescribed medications, dosage amounts, dosage frequency and related precautions and instructions in connection with the administration thereof is very desirable.

Modem computer technology has several attributes that would seem to make it applicable to solving these problems. That is, present day computers can manage very large amounts of data and can make enormous numbers of calculations extremely fast. However it has not been until extremely recently that computer technology having the capability to deliver real-time customized reminders to individual patients with respect to medical prescriptions has even been contemplated.

Thus there is a continuing need for a system and method that can track diverse medications, their amounts and administration regimens for a large number of people and to deliver instantaneously, real-time and/or batch-based, customized reminders addressed to specific individuals to take their medicines. It is also desirable to provide a prescription reminding system that functions without the need for loading of information or reminder schedule programming by the patient.

Efforts by many health institutions to use telephone calls to remind patients throughout the day to take prescribed medications are often found to be intrusive and have been met with limited success. The well-designed study titled *The effects of postal and telephone reminders on compliance with pravastatin therapy in a national registry: results of the first myocardial infarction risk reduction program* [Guthrie, R M. Clin Ther. 2001 June; 23(6): 970–80] indicated that telephone reminders did not improve compliance. These studies have also been extended to the utilization of cell phones. While the success factors are still being studied, it is expected that improved compliance will be negatively influenced by the facts (a) that many senior patients do not routinely carry a cell phone, and (b) that those who have a cell phone frequently leave the phone turned off. There is thus also need for a prescription reminding service that can successfully improve compliance without causing the patients to significantly change behavior, e.g. by buying and using cell phones.

SUMMARY OF THE INVENTION

Accordingly the present invention provides a medical alerting system comprising a connectivity server including a digital computer, a supervisory computer program continuously running on the connectivity server, a medication database in machine-readable form stored in computer memory accessible in real-time by the supervisory computer program and comprising medical records for patients each of whom has a unique patient identifier, and which medical records comprise regimens for administration of one or more medications or therapies prescribed for the patients, a wide area network subsystem adapted to wirelessly transmit into a preselected geographic area real-time alerting signals of electromagnetic radiation corresponding to directive signals provided from time-to-time by the connectivity server, and a plurality of portable receivers assigned uniquely to individual patients and operative to receive the alerting signals in real-time, each receiver comprising (a) an electronic filter adapted to selectively accept alerting signals directed to only the one individual patient assigned to the receiver, (b) a visual display unit, and (c) an interpreter system operative to provide to the visual display unit a human-readable message which corresponds to an alert signal, in which the supervisory computer program is operative to use the medical records obtained from the medication database to generate directive signals corresponding to events in the regimens of respective patients.

There is also provided a process for alerting a patient about administration of a prescribed medication or therapy comprising (A) providing a system comprising (i) a connectivity server including a digital computer, (ii) a supervisory computer program continuously running on the connectivity server, (iii) a medication database in machine-readable form stored in computer memory, (iv) a wide area network subsystem adapted to wirelessly transmit into a preselected geographic area real-time signals of electromagnetic radiation, and (v) a plurality of portable receivers operative to receive signals of electromagnetic radiation transmitted by the wide area network subsystem, and having a visual display unit, (B) allotting a unique identification code to each of a plurality of individuals, (C) associating each individual with a different portable receiver, (D) storing in the medication database medical records for each individual comprising the identification code and regimens for administration of one or more prescribed medications or therapies for the individual, (E) operating the supervisory computer program on the medical records to determine a scheduled time that a regimen calls for a scheduled administration of medication or therapy to a patient among the individuals, (F) generating from the connectivity server to the wide area network subsystem an instruction for the patient corresponding to the scheduled administration of medication or therapy for the patient, (G) wirelessly transmitting throughout the preselected geographic area via the wide area network subsystem an alerting signal of electromagnetic radiation corresponding to the instruction, (H) filtering the alerting signal by the portable receivers such that only the receiver associated with the patient accepts the alerting signal corresponding to the instruction for the patient, and (I) displaying a visually perceptible message on the visual display unit of the portable receiver associated with the patient.

DETAILED DESCRIPTION OF THE INVENTION

Figure 1:
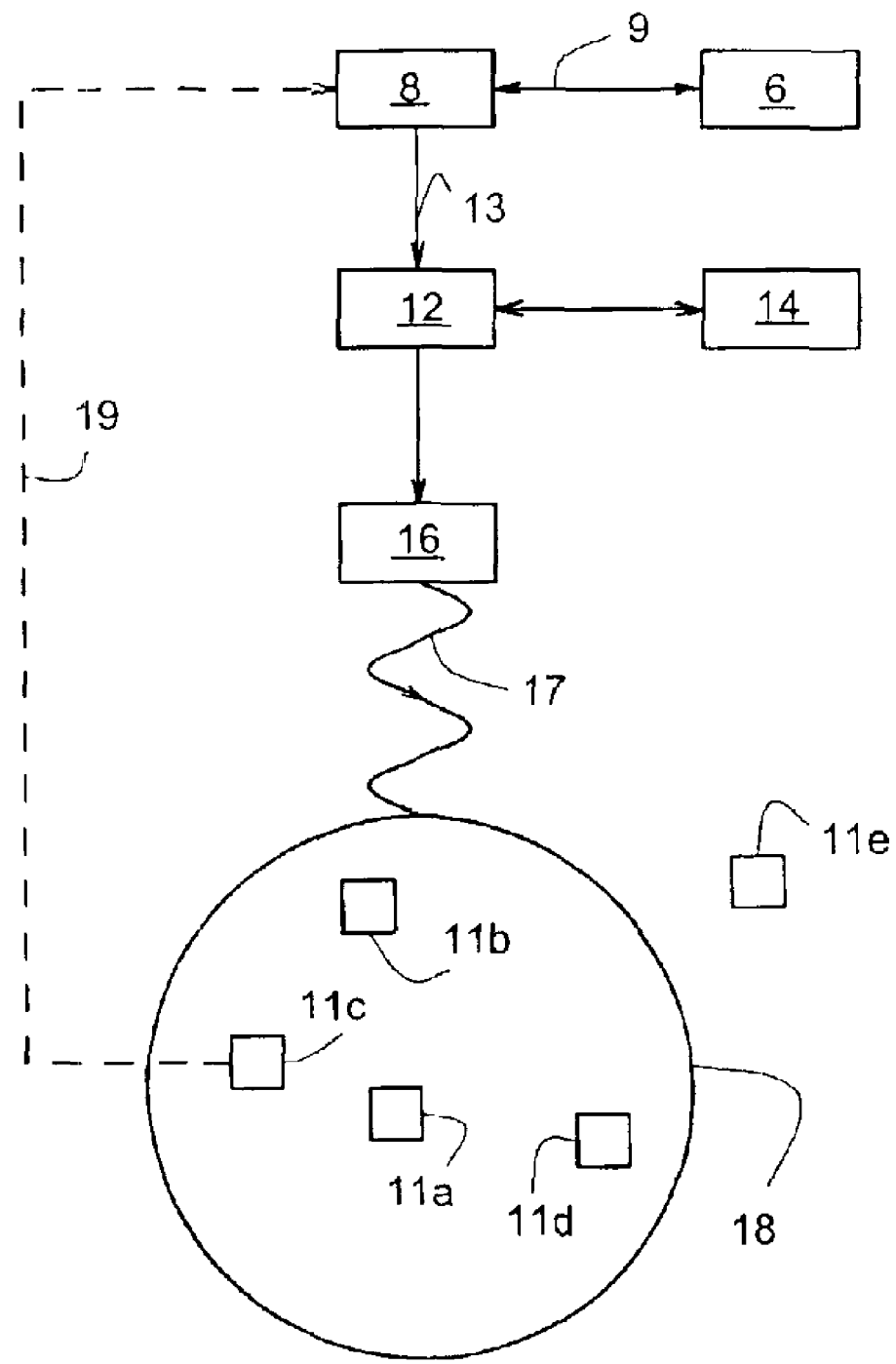
FIG. 1 is a schematic diagram showing the interrelationships between the components of the novel medical alerting system.

In a basic aspect the present invention pertains to a system of computerized components and peripherals set up to send out real-time reminders to patients about their prescription medication regimens. The reminders are customized so that each patient obtains reminders directed to, tailored specifically for and received solely by the specific individual patient to whom a particular reminder relates. The reminders are made to the patient in real-time, that is, near the actual time that the patient is due to take an action which is the subject of the reminder.

The interrelationships between the components of the system may be understood with reference to FIG. 1. Central to the novel medical alerting system is a connectivity computer server 12. The connectivity server, in addition to customary conventional accessories includes an electronic digital computer and a supervisory computer control program ("supervisory program"). The supervisory program generally manages the ongoing operation of the whole system.

The supervisory program draws upon a medication database 14 as a resource. The medication database is a computer software application which contains the information that describes the systematic plans designed by health care professionals to improve and maintain the health of the patients. The term "regimen" is used herein to mean the subset of information in these plans that identifies with specificity at least the name, dose amount, dose frequency and cautionary or advisory information about the administration of medication or therapy according to a patient's plan. The medication database has the regimens stored in machine-readable code that is accessible at any time by the supervisory program.

The connectivity server 12 is linked to a wide area network subsystem 16. This component allows the connectivity server to disseminate electronic information wirelessly in real-time throughout a defined geographic region 18. The electronic information is broadcast in the form of electromagnetic radiation signals 17, e.g., radiofrequency wave transmissions. The transmissions from the wide area network subsystem are detected by a plurality of portable receiving devices 11a–11d. Each portable receiving device is uniquely associated with one patient from among the individuals who are enrolled to receive reminders. That is, each patient is assigned to one and only one distinctly identifiable portable receiving device. The wide area network subsystem transmits signals and the portable receiving devices receive the signals in a manner that those signals addressed to a particular patient are accepted only by the portable receiving device associated with that patient. Accordingly, every patient only receives signals addressed to his or her own receiving device and thus only obtains his or her own reminders. Patients do not retrieve signals addressed to other patients.

The portable receiving devices are light weight, compact and self-powered by an onboard battery. It is contemplated that the receivers will be about the size of a conventional wristwatch. The patient can carry or wear the device as an item of jewelry or clothing accessory such as watch on a wrist band, a pendant on a necklace, a fob on a key chain, a pocket watch, for example. The device can be combined with other utilitarian personal accessories items including for example, pocket knives, pagers, cellular telephones, belt buckles, hand-held computers and the like.

The portable receiving devices can use a variety of methods for alerting the patient about a medication or therapy reminder, such as audible alarm or announcement, vibration alarm, visual messaging and combinations thereof. Preferably, the device should have a visual display unit on which visually perceptible messages pertaining to the administration of medication or therapy can be made to appear for inspection by the patient. The visual display unit preferably has a display screen of about the size of a conventional watch face. It is contemplated that the patient will look at the visual display unit either from time to time at the patient's discretion or when prompted by an alarm emanating from the device. The patient will review visually perceptible messages appearing on the display unit and be reminded thereby to attend to administration of medication or therapy as indicated.

A preferred technology for a wide are network subsystem and personal receiver device utilizes the so-called Direct-Band Network and Smart Personal Objects Technology (the latter occasionally referred to as "SPOT") developed by Microsoft Corporation and others. The Direct Band Network is a continuous broadcast network, contemplated to be nationwide in the United States and Canada The Direct Band Network uses FM radio subcarrier frequencies to transmit information using radio protocols designed to make communication with devices that have SPOT functionality.

A SPOT device comprises a miniaturized radio frequency signal receiver, an application chip and operating software. It has small power consumption requirements, portable power supplies, and are small in size and weight to enhance portability. In a particularly preferred embodiment for use in accordance with this invention, the SPOT device will have the appearance of a conventional watch. It will have date and time-keeping functions and will include a visual display that preferably exploits liquid crystal technology to provide messages directed to the patient in possession of the particular SPOT device. The preferred SPOT device has an interactive, contact sensitive visual display unit, sometimes referred to as a "touch screen" technology. Thus the patient can acknowledge and scroll between pages of displayed information by touching selected portions of the screen. The SPOT operating software controls the display of information, touch sensitive and the interactive user interface.

Each SPOT device is uniquely addressable, such that signals transmitted to from the DirectBand Network can be directed exclusively to specific SPOT devices. The SPOT device thus has ability to receive a real-time radio frequency transmission initiated by the connectivity server and transmitted via the DirectBand Network directly to one particular SPOT device. The signal received by the SPOT device is contemporaneously logged by the onboard operating software which causes a visually perceptible message of appropriate human understandable content to appear on the visual display unit. The SPOT device does not need to receive a signal contemporaneously with every alert or alarm shown or sounded on the display unit. For example, as will be more fully described below, a signal could be sent and received from time to time for the purpose of updating the on-board alert schedule to assure that the on-board schedule is up to date so that the schedule can be relied even when the bearer takes a SPOT device outside of a wide area network system.

In one aspect, the SPOT device displays a human understandable message that corresponds directly to the content of the signal transmitted by the wide area network subsystem. For example, the connectivity server may initiate a reminder for the patient to take a 50 mg dose of acetomenaphen at 10:00 am and the SPOT device will respond in a manner that comprises producing the text message: "TAKE 50 MG ACETOMENAPHEN AT 10:00 AM" on the visual display unit.

In another aspect the SPOT device optionally comprises an onboard memory bank that has a plurality of storage locations. A library of encoded displays that correspond to a variety of visually perceptible messages can be stored in these locations. Preferably the memory bank will be non-volatile such that the information content will not be lost when power for the SPOT device is deactivated from time to time for example for maintenance or power conservation purposes. The content of the storage locations can be loaded batchwise, i.e., many at one time, so that the SPOT device can be initialized with a standard set of messages prior to distribution of the device to a particular patient. It is also contemplated that the content of stored memory locations can be downloaded in real time as occasionally desired to update the onboard memory bank. The operating software for the SPOT device is enabled to select from among the encoded display information stored in memory and to cause messages corresponding to the selected information to appear on the display unit at selected times according to a schedule that is consistent with the patient's regimens for scheduled administration of medication or therapy. This functionality can be programmed to continue according to a calendar defined by parameters also stored in onboard memory and interpreted by the SPOT operating software.

The SPOT device thus provides the novel medical alerting system with the advantageous ability to maintain a schedule of medical reminders for a patient even when the SPOT device is unable to receive current signals from the wide area network subsystem. This situation is illustrated schematically in FIG. 1 with reference to portable receiver device 11e. This device has been taken outside of the area of coverage 18 of the wide area network subsystem 16 and is too remote to receive signals 17 initiated by the connectivity server. However, reminder messages will continue to display at appropriate times on that SPOT device. When receiver 11e returns to coverage area 18, it will commence to receive current signals and will have its onboard memory updated thereby. The operating software will interpret the updated information and will modify the reminders for the patient accordingly. The coverage area for a wide area network subsystem can be limited as shown in FIG. 1 as a result of absence of relay transmission antennae is certain geographic locales, interference, temporary subsystem shutdowns for maintenance and similar reasons.

SPOT devices are presently contemplated to have receive-only capability. Hence an embodiment of the novel medical alerting system that utilizes present generation SPOT devices will be a one-way communication system. That is, the flow of communication will be from the connectivity server to the SPOT devices. In still another aspect, the patient can provide feedback information to the supervisory computer program on the connectivity server. In this way the patient can maintain a record of medication and treatment regimen activities completed, delayed and/or missed. The supervisory computer program can account for deviations from the desired schedule and can make appropriate changes to the schedule so as to provide the patient with the most effective use of medications and therapies. Another potential mode for feedback information can be to require the patient to log a response within a specified time of a scheduled regimen event. For example, a diabetes patient could be required to provide feedback about diet or insulin concentration at specified times. If the patient does not report, the connectivity server can be made functional to alert health care providers or emergency contact personnel.

The capability to provide feedback is represented schematically in FIG. 1 by dashed line 19. It is seen that the novel medical alerting system includes a remotely accessible interface 8. The interface can communicate with the connectivity server 12 via communications link 13. Typical types of remotely accessible interfaces that can be used are an interactive voice response telecommunication portal and an internet portal. Thus, the patient having desire to communicate pertinent information to the connectivity server can place a telephone call to a predetermined number and then enter identification and substantive information via voice or telephone keypad response to an interactive prompting service. In another embodiment the patient can access an internet website provided for this purpose. When connected to the internet portal, the patient can log into the system with pre-assigned password and then can type or otherwise provide pertinent information. Internet access can be by conventional methods such as telephone dial up service, local wireless wide area networks for internet pick up and the like.

Pre-approved, third parties 6 can also access the connectivity server. For example, qualified medical advisors such as physicians and pharmacists can change the regimens for particular patients. These persons can also obtain reports about the existing regimens and feedback information provided by the patients via link 9 to the remotely accessible interface.

The portable receiving devices, especially those utilizing SPOT functionality, have one or more manually operable switches, sometimes referred to as "hard keys". These hard keys provide an interface for the patient to access the onboard operating software to obtain the benefit of selected services. For example, a hard key can be programmed to direct the operating software to display on the visual display unit a report of all of the regimens for which the patient is then presently prescribed. This is particularly valuable when the patient desires to explain to a health care provider the identities and dosages of all medications that the patient is currently taking. The need to have a comprehensive list of medications can be important in an emergency situation to simplify routine hospital admission processing or the like. When a feedback link 19 and remotely accessible interface 8 is provided, the patient can direct the connectivity server to prepare reports in printed or electronic form for similar purposes.

Hard keys can also be used to select between modes of operation (e.g., timekeeping function, medical alert function, report creating function), to paint the display unit screen with successive pages of information, to set display or system preferences, and the like.

Operation and various features of the medical alerting system can be better understood from the following illustrative exemplary process description. A medical alerting system provider establishes a connectivity server with output link to a DirectBand Network wide area network subsystem. The network subsystem can transmit radio frequency signals wirelessly everywhere within a specified territory, for example, the state of Connecticut. The connectivity server can be located remotely from the DirectBand coverage area. A pharmacy that has retail prescription service in maintains a medication database for it customers. The database includes medical records for each customer and the records contain the name, dosage, frequency of administration, precautionary advice concerning administration of medications, for each customer. Each customer is uniquely identified in the medication database by an indexing database field, e.g. customer number, that is assigned by the medication database administrator. The medical records are provided to the pharmacy by physicians who have prescription writing authority with respect to the pharmacy customers.

Customers desiring to utilize the medical alerting service, subscribe with the medical alerting system provider. The customer can subscribe directly with the medical alerting system provider but it is contemplated that subscription activation is most conveniently performed by the pharmacy at the time the customer places the prescription order. When a patient subscribes to the medical alerting system, a SPOT device having a unique identification code, e.g., a serial number, is delivered to the patient. That patient's medication database customer number is associated with the serial number and the cross-referenced identification information is placed in memory accessible to the supervisory computer program on the connectivity server.

The SPOT device given to the patient is a unit having a wrist band and is intended to be worn and to appear like an ordinary wrist watch. As delivered to the patient, the SPOT device has a nonvolatile memory bank of storage locations in which reside a library of alert messages, dosage measurements, precautionary statements and like information pertaining to the administration of medications and therapies. For example, the memory locations can be programmed with coded instructions suitable for causing messages to appear on the visual display unit such as the names of most commonly prescribed pharmaceuticals, typical units of measure, e.g., "drops", "tablespoons", "tablets", "milligrams", "capsules", and phrases, e.g., "take every _____ hours", "take with food", "do not operate heavy machinery for _____ hours after taking", and the like. Based on information received via The DirectBand Network, the SPOT device operating software is able to retrieve selected of these coded message components, incorporate appropriate received information and assemble text messages on the display screen in preselected format. The assembled text messages contain reminders about various aspects of the patient's regimen that are presented in a visually perceptible manner that the patient can understand and follow.

The supervisory computer program continuously monitors the current date and time. Periodically, and preferably at high frequency of about 1 cycle per minute or more frequently, the supervisory computer program polls the medication database. The medication database is stored on a server computer maintained by the retail pharmacy. For this purpose, the connectivity server maintains a continuous connection with the database server computer or establishes temporary connections from time to time as dictated by the cycle frequency. During the polling step, the supervisory computer program queries the medication database to obtain the most recent values of medication database records for the patients who have subscribed to the medical alerting system service. The supervisory computer program maintains an up-to-date database, preferably on the connectivity server, which contains the cumulatively current records for each subscribed patient.

The supervisory computer program parses the medication database information in a manner that enables the fabrication of a schedule for the administration of medications and therapies for each patient. For example, the program determines that patient "R. Jones", identified by customer number "X5332J" is scheduled to take 80 mg of blood pressure regulation medication supplied in 40 mg tablets daily at 8:00 pm. From available resource libraries, the supervisory program also knows the shape, color, distinctive characteristics, and other information, e.g., hazardous interactions with other pharmaceuticals, foods etc. for this medication. The supervisory computer program creates a set of machine-readable commands that can be transmitted and understood by a SPOT device. The command set includes all of the information pertinent to the prescribed regimen for administration of this pharmaceutical to patient X5332J. The set is parsed in such away that the SPOT operating system can use the commands ultimately to produce a meaningful reminder in understandable terms for the patient. When the medication has a unique form, such as in this example, the supervisory computer program includes in the command set an image file showing a view of an actual sample of the medication. Here, the image file contains a image of a round, yellow tablet bearing the manufacturer's distinctive molded imprint.

The supervisory computer continuously compares information received from the medication database to information in the regimen-defining command sets. When medication database information is new or different from that in the existing command set for a particular patient, the supervisory computer program updates the outdated command sets and instructs the connectivity server to send the updated command sets to respective SPOT devices. Accordingly, the connectivity server directs transmission of the updated command sets via the DirectBand Network wide area network subsystem.

Each command set is addressed to a particular SPOT device. Thus the regimen for taking 80 mg of blood pressure regulation medication is sent to the SPOT device associated with patient R. Jones, who is identified by number X5332J. The command set is broadcast throughout the coverage area by the wide area network subsystem. However, all SPOT devices except the one associated with identification number X5332J reject receipt of the exemplary command set. Only R. Jones' SPOT device accepts the command set and reacts to it, provided that this SPOT device is within the coverage area when the command set is broadcast. Conversely, R. Jones' SPOT device rejects all other command sets and does not react to command sets addressed to other patients.

When received, the command set is stored onboard and interpreted by the SPOT device. The interpreted command set provides the SPOT device with a real-time schedule for displaying predetermined messages on the display unit. The messages incorporate coded instructions that had been previously programmed into memory locations, and new text and/or images recently received by radio frequency transmission via the wide area network subsystem as applicable. With respect to the present representative example, the SPOT receiver has onboard instructions that call for the display of a reminder to take two 40 mg tablets of the specified blood pressure regulation medication at 8:00 pm every day.

The default display of the SPOT device presents a watch face with current time showing. Preferably, the display area includes a location where a symbol indicates that the scheduled regimen has been updated by receipt of a new command set. When the patient first notices the appearance of the new command set receipt symbol, the patient responds by pressing a hard key or the "touch screen". The SPOT device responds by replacing or supplementing the current time display with messages and/or images that describe the specific changes on the display unit. The patient can also manipulate the hard keys to cause the display unit to show the whole current regimen. The patient's attention optionally can be brought to the arrival of a new command set by an audible or tactile (i.e., vibration) signal. After acknowledging the receipt of a new command set, the patient can manipulate the hard keys or touch screen to return the current time display to the visual display unit of the SPOT device.

The SPOT device continuously compares the current date and time to times for events scheduled to occur in the regimen as defined by the currently interpreted command set. At an appropriate lead time prior to a scheduled event, the default time display is overwritten or supplemented with a visually perceptible display of a reminder message on the visual display unit. The reminder message may contain multiple pages. For example, the first page reminds the patient about the name of the medication and the time of scheduled administration. A next page describes the total dose and the number of individual units of medication to be administered. A next page shows an image of a specimen of the actual medication. This helps to assure that the patient takes the correct medicine at the proper time. Other pages contain instructions and or cautions related to the administration of the medication, such as "causes drowsiness". The patient uses hard keys and/or touch screen functionality to scroll through the pages and repeat the reminder as many times as necessary. Lastly, the patient returns the display unit to exhibit the default current time display and proceeds to follow the prescribed regimen consistently with the reminder.

The user can set preferences associated with the reminders. That is, the hard keys and/or touch screen functionality is programmed to let the patient control the amount of lead time before a scheduled event that the reminder first appears. The patient can also set up the SPOT to provide a supplemental audible or tactile alarm signal to call attention to a scheduled event.

Although specific forms of the invention have been selected for illustration in the drawings and the preceding description is drawn in specific terms for the purpose of describing these forms of the invention fully and amply for one of average skill in the pertinent art, it should be understood that various substitutions and modifications which bring about substantially equivalent or superior results and/or performance are deemed to be within the scope and spirit of the following claims.

what is claimed is:

1. A medical alerting system comprising
   a connectivity server including a digital computer,
   a supervisory computer program continuously running on the connectivity server,
   a medication database in machine-readable form stored in computer memory accessible in real-time by the supervisory computer program and comprising medical records for patients each of whom has a unique patient identifier, and which medical records comprise regimens for administration of one or more medications or therapies prescribed for the patients,
   a wide area network subsystem adapted to wirelessly transmit into a preselected geographic area real-time alerting signals of electromagnetic radiation corresponding to directive signals provided from time-to-time by the connectivity server, and a plurality of portable receivers assigned uniquely to individual patients and operative to receive the alerting signals in real-time, each receiver comprising (a) an electronic filter adapted to selectively accept alerting signals directed to only the one individual patient assigned to the receiver, (b) a visual display unit, and (c) an interpreter system operative to provide to the visual display unit a human-readable message which corresponds to an alert signal in which the supervisory computer program is operative to use the medical records obtained from the medication database to generate directive signals corresponding to events in the regimens of respective patients, and in which the interpreter system comprises a standardized database of pre-programmed messages pertinent to regimens for administration of medications or therapies, and in which the interpreter system is operative to select one or more messages to be displayed in response to receipt by the receiver of corresponding alerting signals.

2. The medical alerting system of claim 1 in which the messages comprise the name of a medication or therapy prescribed for the patient, the dose of the medication or therapy to be administered, instructions for the administration of the medication or therapy, and optionally, images of the medication or therapy.

3. The medical alerting system of claim 1 in which the receiver further comprises a manually operable switch and the interpreter system is adapted to provide on the visual display unit one or more messages in a scrolling sequence that present all of the names of the medication or therapy currently prescribed by the regimens for the individual patient assigned to the receiver when the switch is activated.

4. The medical alerting system of claim 1 in which the connectivity server comprises a remotely accessible interface through which real-time modifications to the regimens and/or the supervisory computer program can be made by a person.

5. The medical alerting system of claim 4 in which the interface is selected from the group consisting of an internet portal and an interactive voice response telecommunication portal.

6. The medical alerting system of claim 5 in which the supervisory computer program comprises a report generation module adapted to provide verbally and/or visually perceptible reports of interactively selected information about the regimens for a patient.

7. The medical alerting system of claim 1 in which the wide area network subsystem includes a DirectBand wide area network and the portable receivers comprise smart personal object technology devices.

8. The medical alerting system of claim 1 in which the portable receivers are adapted to be worn on a wrist of the patient in the style of a wrist watch.

9. A process for alerting a patient about administration of a prescribed medication or therapy comprising (A) providing a system comprising
  (i) a connectivity server including a digital computer,
  (ii) a supervisory computer program continuously running on the connectivity server,
  (iii) a medication database in machine-readable form stored in computer memory,
  (iv) a wide area network subsystem adapted to wirelessly transmit into a preselected geographic area real-time signals of electromagnetic radiation, and
  (v) a plurality of portable receivers operative to receive signals of electromagnetic radiation transmitted by the wide area network subsystem, each receiver having a visual display unit and an onboard memory bank in which is stored a library of encoded displays of preselected visually perceptible messages pertaining to administration of medications or therapies (B) allotting a unique identification code to each of a plurality of individuals, (C) associating each individual with a different portable receiver, (D) storing in the medication database medical records for each individual comprising the identification code and regimens for administration of one or more prescribed medications or therapies for the individual, (E) operating the supervisory computer program on the medical records to determine a scheduled time that a regimen calls for a scheduled administration of medication or therapy to a patient among the individuals, (F) generating from the connectivity server to the wide area network subsystem an instruction for the patient corresponding to the scheduled administration of medication or therapy for the patient, (G) wirelessly transmitting throughout the preselected geographic area via the wide area network subsystem an alerting signal of electromagnetic radiation corresponding to the instruction, (H) filtering the alerting signal by the portable receivers such that only the receiver associated with the patient accepts the alerting signal corresponding to the instruction for the patient, (I) displaying a visually perceptible message on the visual display unit of the portable receiver associated with the patient, (J) setting up a calendar of the scheduled administration of prescribed medications or therapies at scheduled times according to initially prescribed regimens for the patient, and (K) near the actual scheduled times in the calendar displaying visually perceptible messages selected from the library which correspond respectively to the scheduled administration of medications or therapies then currently due.

10. The process of claim 9 which comprises utilizing the alerting signal accepted by the portable receiver to display near the actual scheduled time one or more visually perceptible messages about the scheduled administration of medication or therapy then currently due.

11. The process of claim 10 in which the alerting signal contains in machine-readable form a visually perceptible message about the scheduled administration of medication or therapy and the process comprises directing the visual display unit to display near the actual scheduled time the visual perceptible message contain in the alerting signal.

12. The process of claim 9 which comprises repeating steps (E)–(I) periodically.

13. The process of claim 12 in which comprises carrying out steps (F)–(I) near the actual scheduled time of the corresponding scheduled administration of medication or therapy.

14. The process of claim 9 in which setting up the calendar comprises utilizing the alerting signal accepted by the portable receiver.

15. The process of claim 14 which comprises utilizing the alerting signal accepted by the portable receiver to modify the calendar from time to time, thereby displaying on the visual display unit near the actual scheduled times visually perceptible messages selected from the library which correspond respectively to the scheduled administration of medications or therapies then currently due according to the modified calendar.

16. The process of claim 9 further comprising the step of changing the determination of scheduled time or scheduled administration of medication or therapy according to adjustments made from time to time to the regimens for a patient.

17. The process of claim 16 which comprises using an internet portal or an interactive voice response telecommunications portal to change the medical records.

18. The process of claim 17 which comprises using information provided by the patient to change the determination of scheduled time or scheduled administration of medications or therapies.

19. The process of claim 9 which further comprises from time to time printing a report for a patient comprising the prescribed regimens for administration of medications or therapies for the patient.

20. The process of claim 9 in which the wide area network subsystem comprises a DirectBand wide area network.

21. The process of claim 9 in which the portable receivers utilize Smart Personal Objects Technology and are adapted to be worn on a wrist of an individual in the style of a wrist watch.

* * * * *